US010477127B2

(12) United States Patent
Blanquart

(10) Patent No.: US 10,477,127 B2
(45) Date of Patent: Nov. 12, 2019

(54) WHITE BALANCE AND FIXED PATTERN NOISE FRAME CALIBRATION USING DISTAL CAP

(71) Applicant: DePuy Synthes Products, Inc., Raynham, MA (US)

(72) Inventor: Laurent Blanquart, Westlake Village, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 3 days.

(21) Appl. No.: 15/351,222

(22) Filed: Nov. 14, 2016

(65) Prior Publication Data

US 2017/0064231 A1  Mar. 2, 2017

Related U.S. Application Data

(63) Continuation of application No. 14/214,791, filed on Mar. 15, 2014, now Pat. No. 9,492,060.

(60) Provisional application No. 61/791,186, filed on Mar. 15, 2013.

(51) Int. Cl.
| | |
|---|---|
| *A61B 1/06* | (2006.01) |
| *H04N 5/365* | (2011.01) |
| *H04N 9/73* | (2006.01) |
| *A61B 1/00* | (2006.01) |
| *A61B 5/04* | (2006.01) |
| *H04N 5/225* | (2006.01) |
| *H04N 9/04* | (2006.01) |
| *H04N 13/239* | (2018.01) |

(52) U.S. Cl.
CPC ....... *H04N 5/3655* (2013.01); *A61B 1/00006* (2013.01); *A61B 1/00009* (2013.01); *A61B 1/00057* (2013.01); *A61B 1/00137* (2013.01); *A61B 1/06* (2013.01); *A61B 5/04* (2013.01); *H04N 5/2256* (2013.01); *H04N 9/045* (2013.01); *H04N 9/735* (2013.01); *H04N 13/239* (2018.05); *H04N 2005/2255* (2013.01); *H04N 2209/044* (2013.01)

(58) Field of Classification Search
None
See application file for complete search history.

(56) References Cited

U.S. PATENT DOCUMENTS

| | | | |
|---|---|---|---|
| 4,433,675 A | 2/1984 | Konoshima | |
| 5,187,572 A | 2/1993 | Nakamura et al. | |
| 5,196,938 A | 3/1993 | Blessinger | |
| 5,241,170 A | 8/1993 | Field, Jr. et al. | |

(Continued)

FOREIGN PATENT DOCUMENTS

| | | | | |
|---|---|---|---|---|
| EP | 2018824 A1 | * | 1/2009 | ........... A61B 5/0071 |
| EP | 2018824 B1 | * | 7/2010 | ........... A61B 5/0071 |
| JP | 2005-211231 | | 8/2005 | |

OTHER PUBLICATIONS

Computer generated English translation of JP 2006-314616.

*Primary Examiner* — William C Vaughn, Jr.
*Assistant Examiner* — Joseph Daniel A Towe
(74) *Attorney, Agent, or Firm* — Terrence J. Edwards; TechLaw Ventures, PLLC

(57) ABSTRACT

The disclosure extends to methods, systems, and computer program products for producing an image in light deficient environments and correction of white balance and/or fixed pattern noise at startup or at any other time during a procedure.

34 Claims, 9 Drawing Sheets

(56) References Cited

U.S. PATENT DOCUMENTS

| | | |
|---|---|---|
| 5,748,234 A | 5/1998 | Lippincott |
| 5,757,011 A | 5/1998 | Whitebook et al. |
| 5,784,099 A | 7/1998 | Lippincott |
| 5,868,666 A | 2/1999 | Okada et al. |
| 6,181,830 B1 | 1/2001 | Sato |
| 6,272,269 B1 | 8/2001 | Naum |
| 6,331,156 B1 | 12/2001 | Haefele et al. |
| 6,485,414 B1 | 11/2002 | Neuberger |
| 6,690,466 B2 | 2/2004 | Miller et al. |
| 6,692,431 B2 | 2/2004 | Kazakevich |
| 6,899,675 B2 | 5/2005 | Cline et al. |
| 6,921,920 B2 | 7/2005 | Kazakevich |
| 6,961,461 B2 | 11/2005 | MacKinnon et al. |
| 6,999,118 B2 | 2/2006 | Suzuki |
| 7,037,259 B2 | 5/2006 | Hakamata et al. |
| 7,189,226 B2 | 3/2007 | Auld et al. |
| 7,258,663 B2 | 8/2007 | Doguchi et al. |
| 7,540,645 B2 | 6/2009 | Kazakevich |
| 7,544,163 B2 | 6/2009 | MacKinnon et al. |
| 7,545,434 B2 | 6/2009 | Bean et al. |
| 7,794,394 B2 | 9/2010 | Frangioni |
| 8,100,826 B2 | 1/2012 | MacKinnon et al. |
| 8,675,980 B2 | 3/2014 | Liege et al. |
| 8,736,007 B2 | 5/2014 | Wu et al. |
| 2001/0030744 A1 | 10/2001 | Chang |
| 2003/0222997 A1* | 12/2003 | Iketani ............... H04N 5/20 348/255 |
| 2004/0109488 A1 | 6/2004 | Glukhovsky et al. |
| 2004/0135209 A1 | 7/2004 | Hsieh et al. |
| 2005/0234302 A1 | 10/2005 | MacKinnon et al. |
| 2006/0069314 A1 | 3/2006 | Farr |
| 2008/0045800 A2 | 2/2008 | Farr |
| 2009/0012361 A1 | 1/2009 | MacKinnon et al. |
| 2009/0046180 A1 | 2/2009 | Shibano et al. |
| 2009/0057559 A1* | 3/2009 | Koyama ............... G01J 3/02 250/340 |
| 2009/0160976 A1 | 6/2009 | Chen et al. |
| 2009/0171159 A1* | 7/2009 | Jorgensen ............ A61B 1/05 600/139 |
| 2009/0225158 A1 | 9/2009 | Kimoto |
| 2009/0234183 A1* | 9/2009 | Abe ............... A61B 1/00165 600/103 |
| 2009/0237498 A1* | 9/2009 | Modell ............ A61B 1/00165 348/65 |
| 2009/0292168 A1 | 11/2009 | Farr |
| 2010/0286475 A1* | 11/2010 | Robertson ........ A61B 1/00096 600/104 |
| 2011/0074943 A1* | 3/2011 | Modell ............ A61B 1/00009 348/77 |
| 2011/0181840 A1 | 7/2011 | Cobb |
| 2011/0237882 A1 | 9/2011 | Saito |
| 2011/0237884 A1 | 9/2011 | Saito |
| 2011/0251484 A1 | 10/2011 | Carpenter et al. |
| 2012/0004508 A1 | 1/2012 | McDowall et al. |
| 2012/0041267 A1 | 2/2012 | Benning et al. |
| 2012/0071720 A1* | 3/2012 | Banik ............. A61B 1/00059 600/118 |
| 2012/0078052 A1 | 3/2012 | Chenc |
| 2012/0262621 A1 | 10/2012 | Sato et al. |
| 2013/0016347 A1* | 1/2013 | Gono ............... A61B 1/0017 356/243.1 |
| 2013/0030247 A1* | 1/2013 | Kimoto ........... A61B 1/00009 600/109 |
| 2013/0035549 A1* | 2/2013 | Abe ................ A61B 1/0011 600/121 |
| 2013/0093912 A1 | 4/2013 | Uchida |
| 2013/0188144 A1* | 7/2013 | Makihira ............ G01J 4/00 351/221 |
| 2014/0022365 A1 | 1/2014 | Yoshino |
| 2014/0200406 A1* | 7/2014 | Bennett ............. A61B 1/127 600/109 |

* cited by examiner

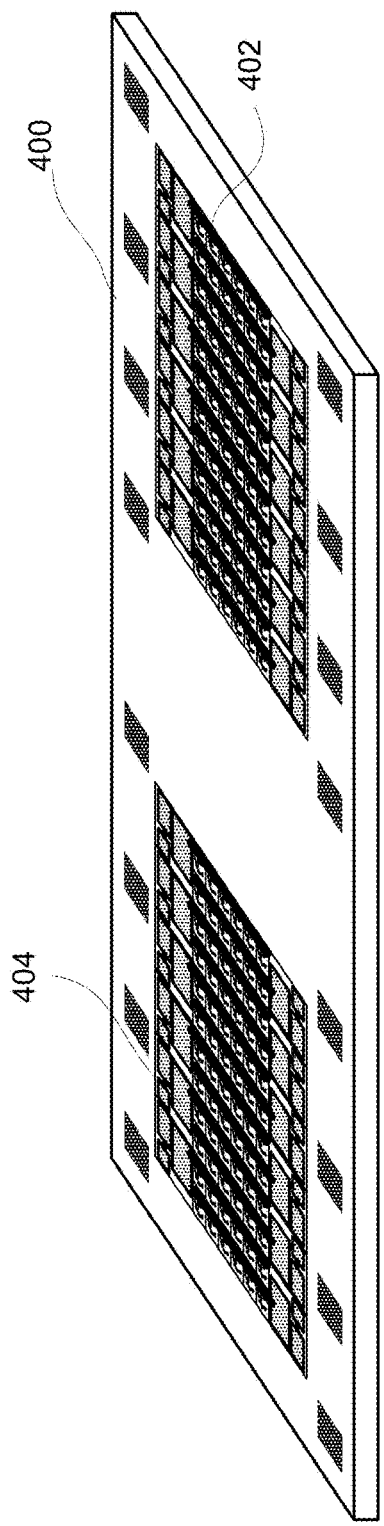
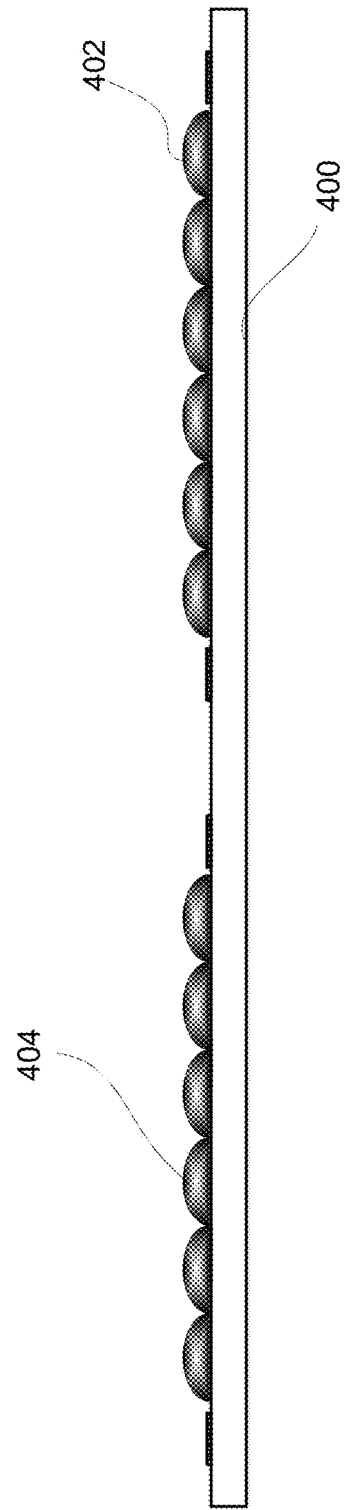
FIG. 4A
FIG. 4B

WHITE BALANCE AND FIXED PATTERN NOISE FRAME CALIBRATION USING DISTAL CAP

CROSS-REFERENCE TO RELATED APPLICATIONS

This application is a continuation of U.S. application Ser. No. 14/214,791, filed Mar. 15, 2014 (now U.S. Pat. No. 9,492,060, issued Nov. 15, 2016) and claims the benefit of U.S. Provisional Application No. 61/791,186, filed Mar. 15, 2013, which are hereby incorporated by reference herein in their entirety, including but not limited to those portions that specifically appear hereinafter, the incorporation by reference being made with the following exception: In the event that any portion of any of the above-referenced applications are inconsistent with this application, this application supersedes above-referenced applications.

STATEMENT REGARDING FEDERALLY SPONSORED RESEARCH OR DEVELOPMENT

Not Applicable.

BACKGROUND

Advances in technology have provided advances in imaging capabilities for medical use. One area that has enjoyed some of the most beneficial advances is that of endoscopic surgical procedures because of the advances in the components that make up an endoscope.

The disclosure relates generally to electromagnetic sensing and sensors, increasing the color accuracy and reducing the fixed pattern noise. The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings.

FIGS. 4A and 4B illustrate a perspective view and a side view, respectively, of an implementation of a monolithic sensor having a plurality of pixel arrays for producing a three dimensional image in accordance with the teachings and principles of the disclosure;

DETAILED DESCRIPTION

Figure 1:
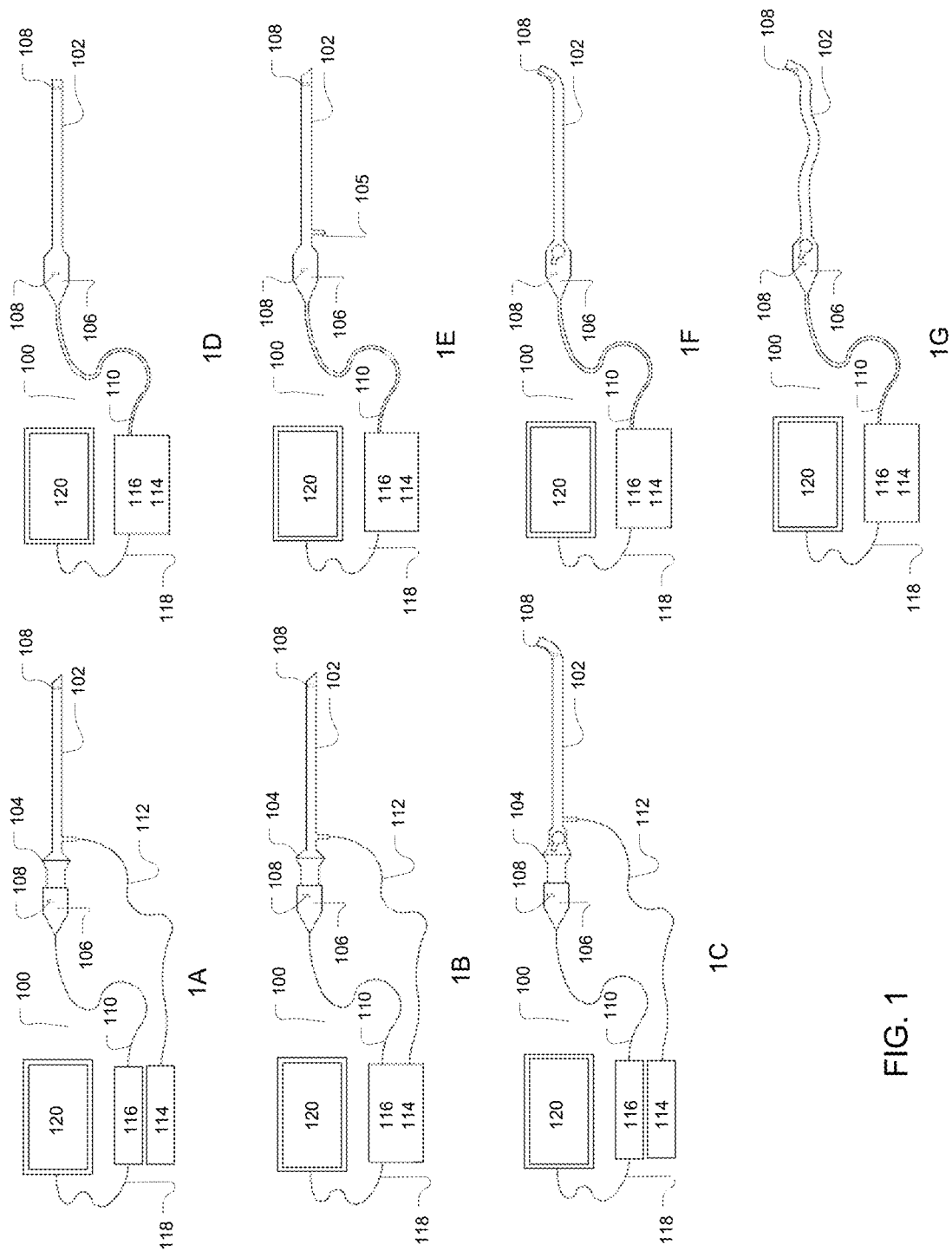
FIG. 1 illustrates various embodiments of an endoscopic system in accordance with the principles and teachings of the disclosure.

The disclosure extends to methods, systems, and computer based products for digital imaging that may be primarily suited to medical applications, and for producing an image in light deficient environments and correction of white balance and/or fixed pattern noise at startup or at any other time during a procedure.

In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA)

thereon so as to filter the incoming electromagnetic radiation into its separate components. In the visual range of the electromagnetic spectrum, such a CFA may be built on a Bayer pattern or modification thereon in order to separate green, red and blue spectrum components of the light.

Modern digital video systems such as those employed for endoscopy incorporate various levels of calibration for the purpose of rendering the image as ideal as possible. In essence, the prime motivation is to mimic the human visual system as closely as possible. Raw color images captured under different types of broad-spectrum illumination (such as sunlight, tungsten filaments, fluorescent lighting, white LEDs etc.), will all have different overall color casts. The human visual system is highly effective in automatically balancing out the biases introduced by the illumination spectra, so as to, e.g., idealize the perception of white and grey scene components. For example, a white sheet of paper always seems white, irrespective of whether the light is, e.g., incandescent or daylight. Raw digital images of a white sheet of paper may appear different shades of off-white under different illuminants, however. To counter this, a digital imaging system, as opposed to the human visual system, must incorporate a white balance process. In fact, most of the process of white balancing is to adjust for the fact that an image sensor response for each color channel is different. The quantum efficiency for a silicon photodiode or other light sensing element is lower for blue photons than for red and green photons for instance.

Endoscopy systems, such as those illustrated in FIG. 1, may have an advantage in that the illuminant does not change during operation, necessitating only a single calibration step. For continuous, broad band illumination-based systems, this is may be accomplished by directing the endoscope at a flat, white target, acquiring one or more images, computing the relative red, green and blue signals and storing the result in memory. During operation, digital gain factors may be applied to the three color channels in the image signal processor (ISP) to compensate for the observed relative responses. If the illumination is provided by pulsing three different wavelengths of monochromatic light (e.g., red, green, and blue), there are two other options for the application of white balance:

Option 1—The light pulse energies are modulated to provide equal response for the red, green, and blue components; and Option 2—The light energies are maximized to take full benefit of the dynamic range of the system, without saturating it. Then the components that have been exaggerated in the optical domain have appropriate digital attenuation factors applied in the ISP.

Option 2, has an advantage for signal-to-noise ratio, since the dominant source of noise is the Poisson uncertainty in photon arrival rate, which scales as the square root of the signal.

The digital processing stages associated with CMOS image sensors are also concerned with correcting for non-idealities that are inherent within the sense technology. One such non-ideality is so-called fixed pattern noise (FPN), which has a strongly detrimental effect on image quality. It arises due to random variations in black level from pixel to pixel. There may also be a column to column component (CFPN) reflecting the analog readout architecture. The degree to which the FPN is offensive to an image signal is dependent on the level of contrast with respect to the true noise sources, such as temporal read noise and photon shot noise. The perception threshold for random pixel FPN is around ¼ of the temporal noise at 60 frames per second, while for CFPN it is around ¹⁄₂₀.

In striving for these targets, a strategy may include compensating for FPN using a dark reference buffer stored on the camera or imaging device, which may be accessible by the ISP. As each physical pixel is sampled by the ISP it may have its dedicated black correction applied. If the illumination is under the fast control of the camera (made possible with LEDs and laser diodes), periodic dark frames may be acquired to keep a running average of the black offsets in order to account for temperature variations. An important component of FPN arises from thermal carrier generation with the photosensitive elements, which has an exponential dependence on absolute temperature.

This disclosure is concerned with a convenient method for the calibration, both initially and at other times during a surgical procedure, for endoscopy systems having full control over their illumination sources. Although an example supported in this disclosure is with a single-use system with sensor at the distal tip, this technique is applicable to re-posable, re-usable and limited use endoscopes, with sensor at the distal tip or within the proximal camera head, with multiple sensor (e.g., for 3D imaging) or single sensor, with rigid or flexible scopes. A set of various system configurations for Minimally Invasive Surgery (MIS) and endoscopy is shown in FIG. 1.

Figure 2A:
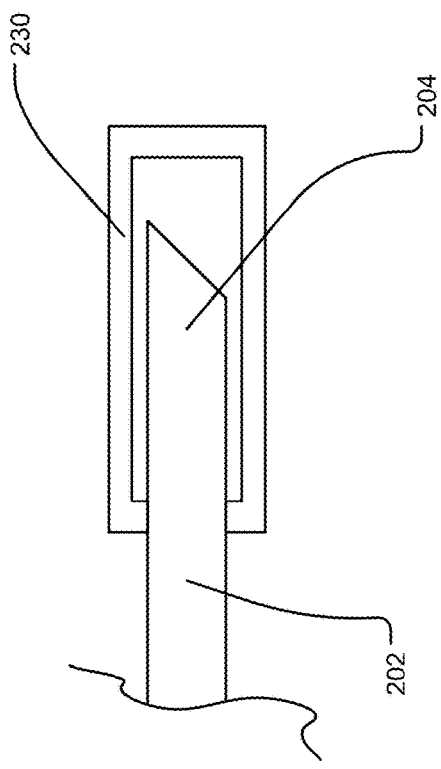
FIG. 2A is an illustration of a distal cap in accordance with the principles and teachings of the disclosure.
Figure 2B:
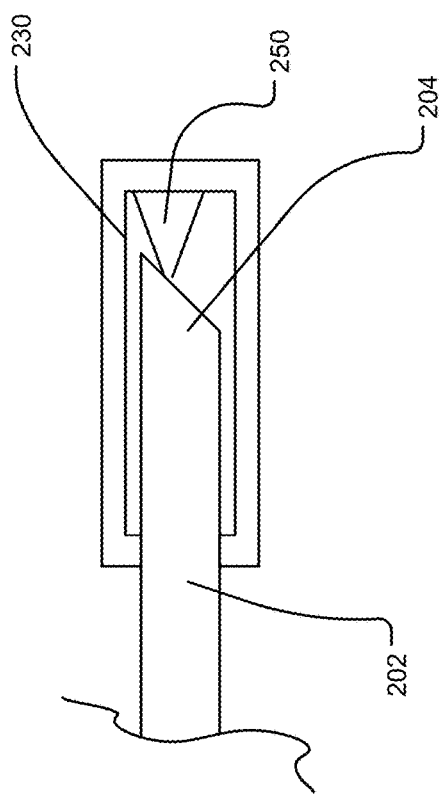
FIG. 2B is an illustration of a distal cap in accordance with the principles and teachings of the disclosure.

As illustrated in FIG. 1, it will be appreciated that a system 100 for digital imaging for use in ambient light deficient environments may comprise a controlled source of electromagnetic radiation 114, an image sensor 108 comprising a pixel array, which senses reflected electromagnetic radiation, optics for continuously focusing a scene onto said pixel array (e.g., optics located distally of the image sensor 108 in the tip of the endoscope), an endoscope comprising a lumen 102 for allowing electromagnetic energies to reach the pixel array, a cap 230 for covering a distal end of the lumen to prevent electromagnetic energies from entering the lumen (see FIGS. 2A and 2B).

It will be appreciated that a dark frame may be created from a single sensing of the pixel array while the cap 230 is covering the distal end of the lumen. It will be appreciated that the cap 230 may be configured, dimensioned, sized and shaped to fit snuggly onto the distal end of the lumen (illustrated best in FIGS. 2A and 2B). The cap may be made of a compliant material. The cap may be opaque to the electromagnetic radiation emitted by an emitter.

The endoscope may be a reusable endoscopic device, a limited use endoscopic device, a re-posable use endoscopic device, or a single-use endoscopic device without departing from the scope of the disclosure.

Continuing to refer to FIG. 1, the system 100 may comprise many different configurations. One example is shown in 1A of FIG. 1, which illustrates an endoscopic system 100 comprising a rigid angled scope 102, an optical coupler 104, a handpiece 106, an image sensor 108, which may be located within the handpiece 106 or distally at a tip of the endoscope 102 as illustrated in dashed lines, an electronic cable 110, a light cable 112, such as a fiber optic cable, a light source 114, a control unit 116, such as a camera control unit (CCU), a video cable 118 and a display 120.

The system configuration shown in 1B of FIG. 1 illustrates an endoscopic system 100 comprising a rigid angled scope 102, an optical coupler 104, a handpiece 106, an image sensor 108, which may be located within the handpiece 106 or distally at a tip of the endoscope 102 as illustrated in dashed lines, an electronic cable 110, a light cable 112, such as a fiber optic cable, a control unit 116, such as a camera control unit (CCU), with an integrated light source 114, a video cable 118, and a display 120.

The system configuration shown in 1C of FIG. 1 illustrates an endoscopic system 100 comprising an articulating scope 102, an optical coupler 104, a handpiece 106, an image sensor 108, which may be located within the handpiece 106 or distally at a tip of the endoscope 102 as illustrated in dashed lines, an electronic cable 110, a light cable 112, such as a fiber optic cable, a light source 114, a control unit 116, such as a camera control unit (CCU), a video cable 118 and a display 120.

The system configuration shown in 1D of FIG. 1 illustrates an endoscopic system 100 comprising a handpiece 106 with an integrated rigid 0 degree scope 102, an image sensor 108, which may be located within the handpiece 106 or distally at a tip of the scope 102 as illustrated in dashed lines, a combined electronic and light cable 110, a control unit 116, such as a camera control unit (CCU) with an integrated light source 114, a video cable 118 and a display 120.

The system configuration shown in 1E of FIG. 1 illustrates an endoscopic system 100 comprising a handpiece 106 with an integrated rigid angled scope 102 and rotation post 105, an image sensor 108, which may be located within the handpiece 106 or distally at a tip of the scope 102 as illustrated in dashed lines, a combined electronic and light cable 110, a control unit 116, such as a camera control unit (CCU) with an integrated light source 114, a video cable 118 and a display 120.

The system configuration shown in 1F of FIG. 1 illustrates an endoscopic system 100 comprising a handpiece 106 with an integrated articulating scope 102, an image sensor 108, which may be located within the handpiece 106 or distally at a tip of the scope 102 as illustrated in dashed lines, a combined electronic and light cable 110, a control unit 116, such as a camera control unit (CCU) with an integrated light source 114, a video cable 118 and a display 120.

The system configuration shown in 1G of FIG. 1 illustrates an endoscopic system 100 comprising a handpiece 106 with an integrated flexible scope 102, an image sensor 108, which may be located within the handpiece 106 or distally at a tip of the scope 102 as illustrated in dashed lines, a combined electronic and light cable 110, a control unit 116, such as a camera control unit (CCU) with an integrated light source 114, a video cable 118 and a display 120.

It will be appreciated that any of the above-identified configurations for an endoscopic system shown in FIG. 1, any combination of the above elements in a different configuration, and any other configuration used for Minimally Invasive Surgery, fall within the scope of this disclosure.

Referring now to FIGS. 2A and 2B, in an embodiment, a single-use system, which may come sterile to the Operating Room (OR), might be equipped with a white cap or an opaque white cap 230 that covers a distal tip 204 of an endoscope 202. Upon opening of the sterile package, the endoscope assembly may be connected to a camera control unit, and the camera control unit may initiate a calibration procedure. During the calibration procedure the system will reach its quiescent and operating temperature and therefore can be optimally calibrated before use. The cap 230 may simply be removed before starting the procedure.

In an embodiment, a manual procedure, where the operator may place a specially designed cap 230 over the endoscope distal tip at any time during a procedure and then instruct the system to perform the calibration.

It will be appreciated that the camera system may acquire a number of frames in darkness, e.g., dark frames or dark frame references, to form the seed dark correction data used for FPN cancellation. The system may turn on the light source, which feeds light out through the endoscopic tip, as it is during normal imaging operation, and acquire another set of frames for the purpose of computing the relative color channel responses. The system may record these responses in memory, retrieve the responses from memory, and use them to compute the appropriate coefficients for white balance. The operator may remove the cap 230 and begin using the system as normal.

FIGS. 2A and 2B show the distal end 204 of the endoscope 202 covered by the cap 230 during the dark calibration and light calibration, respectively. FIG. 2B illustrates the light cone 250 illuminating or showing through the distal end 204 of the endoscope 202 to the cap 230.

It will be appreciated that implementations of the disclosure may comprise or utilize a special purpose or general-purpose computer including computer hardware, such as, for example, one or more processors and system memory, as discussed in greater detail below. Implementations within the scope of the disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked in order to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Figure 3:
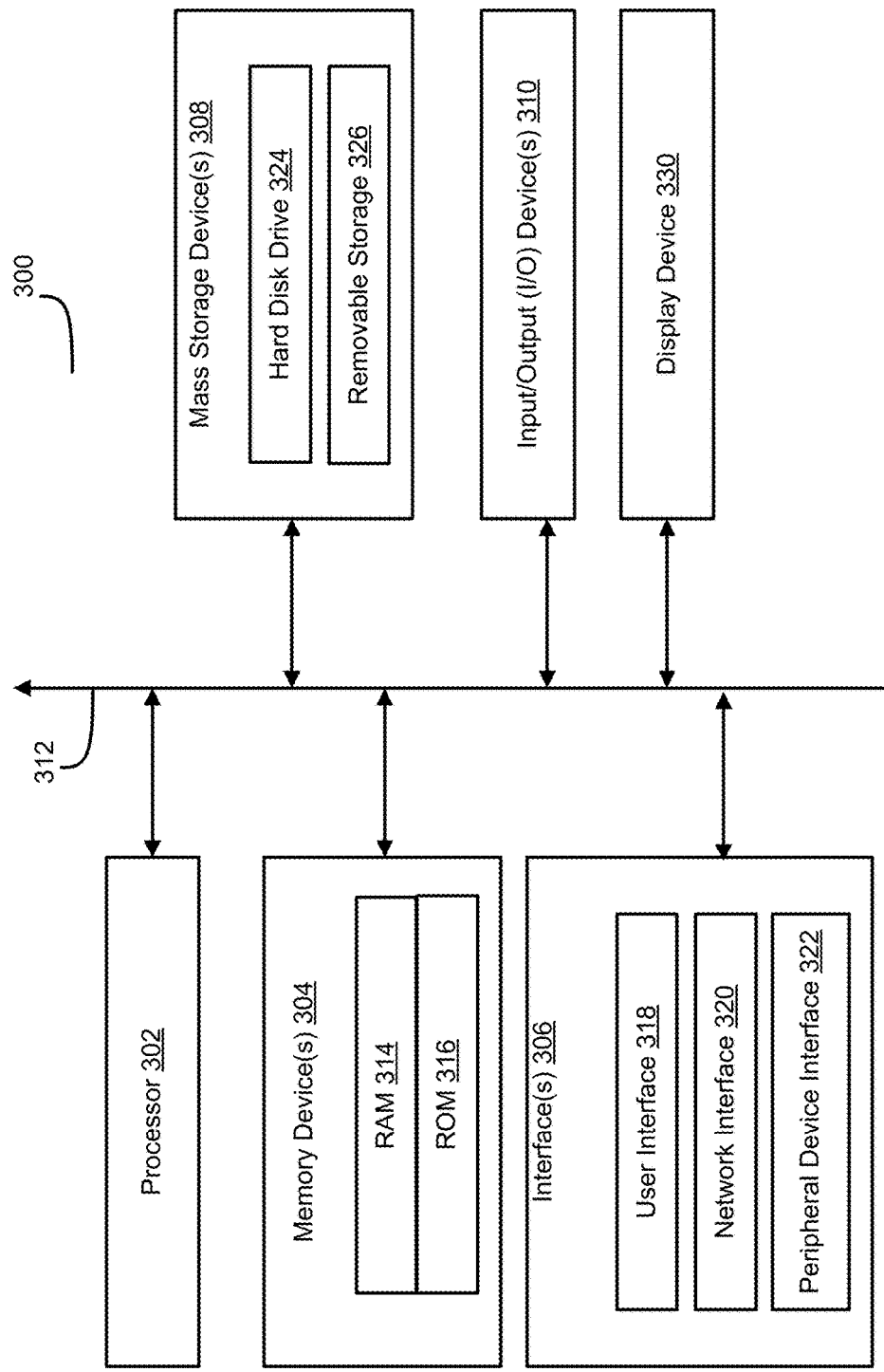
FIG. 3 illustrates a schematic of supporting and enabling hardware in accordance with the principles and teachings of the disclosure.

As can be seen in FIG. 3, various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 3 is a block diagram illustrating an example computing device 300. Computing device 300 may be used to perform various procedures, such as those discussed herein. Computing device 300 can function as a server, a client, or any other computing entity. Computing device can perform various monitoring functions as discussed herein, and can execute one or more application programs, such as the application programs described herein. Computing device 300 can be any of a wide variety of computing devices, such as a desktop computer, a notebook computer, a server computer, a handheld computer, camera control unit, tablet computer and the like.

Computing device 300 includes one or more processor(s) 302, one or more memory device(s) 304, one or more interface(s) 306, one or more mass storage device(s) 308, one or more Input/Output (I/O) device(s) 310, and a display device 330 all of which are coupled to a bus 312. Processor(s) 302 include one or more processors or controllers that execute instructions stored in memory device(s) 304 and/or mass storage device(s) 308. Processor(s) 302 may also include various types of computer-readable media, such as cache memory.

Memory device(s) 304 include various computer-readable media, such as volatile memory (e.g., random access memory (RAM) 314) and/or nonvolatile memory (e.g., read-only memory (ROM) 316). Memory device(s) 304 may also include rewritable ROM, such as Flash memory.

Mass storage device(s) 308 include various computer readable media, such as magnetic tapes, magnetic disks, optical disks, solid-state memory (e.g., Flash memory), and so forth. As shown in FIG. 3, a particular mass storage device is a hard disk drive 324. Various drives may also be included in mass storage device(s) 308 to enable reading from and/or writing to the various computer readable media. Mass storage device(s) 308 include removable media 326 and/or non-removable media.

I/O device(s) 310 include various devices that allow data and/or other information to be input to or retrieved from computing device 300. Example I/O device(s) 310 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 330 includes any type of device capable of displaying information to one or more users of computing device 300. Examples of display device 330 include a monitor, display terminal, video projection device, and the like.

Interface(s) 306 include various interfaces that allow computing device 300 to interact with other systems, devices, or computing environments. Example interface(s) 306 may include any number of different network interfaces 320, such as interfaces to local area networks (LANs), wide area networks (WANs), wireless networks, and the Internet. Other interface(s) include user interface 318 and peripheral device interface 322. The interface(s) 306 may also include one or more user interface elements 318. The interface(s) 306 may also include one or more peripheral interfaces such as interfaces for printers, pointing devices (mice, track pad, etc.), keyboards, and the like.

Bus 312 allows processor(s) 302, memory device(s) 304, interface(s) 306, mass storage device(s) 308, and I/O device(s) 310 to communicate with one another, as well as other devices or components coupled to bus 332. Bus 312 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 300, and are executed by processor(s) 302. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

It will be appreciated that the disclosure may be used with any image sensor, whether a CMOS image sensor or CCD image sensor, without departing from the scope of the disclosure. Further, the image sensor may be located in any location within the overall system, including, but not limited to, the tip of the endoscope, the hand piece of the imaging device or camera, the control unit, or any other location within the system without departing from the scope of the disclosure.

Implementations of an image sensor that may be utilized by the disclosure include, but are not limited to, the following, which are merely examples of various types of sensors that may be utilized by the disclosure.

Referring now to FIGS. 4A and 4B, the figures illustrate a perspective view and a side view, respectively, of an implementation of a monolithic sensor 400 having a plurality of pixel arrays for producing a three dimensional image in accordance with the teachings and principles of the disclosure. Such an implementation may be desirable for three dimensional image capture, wherein the two pixel arrays 402 and 404 may be offset during use. In another implementation, a first pixel array 402 and a second pixel array 404 may be dedicated to receiving a predetermined range of wave lengths of electromagnetic radiation, wherein the first pixel array 402 is dedicated to a different range of wave length electromagnetic radiation than the second pixel array 404.

Figure 5A:
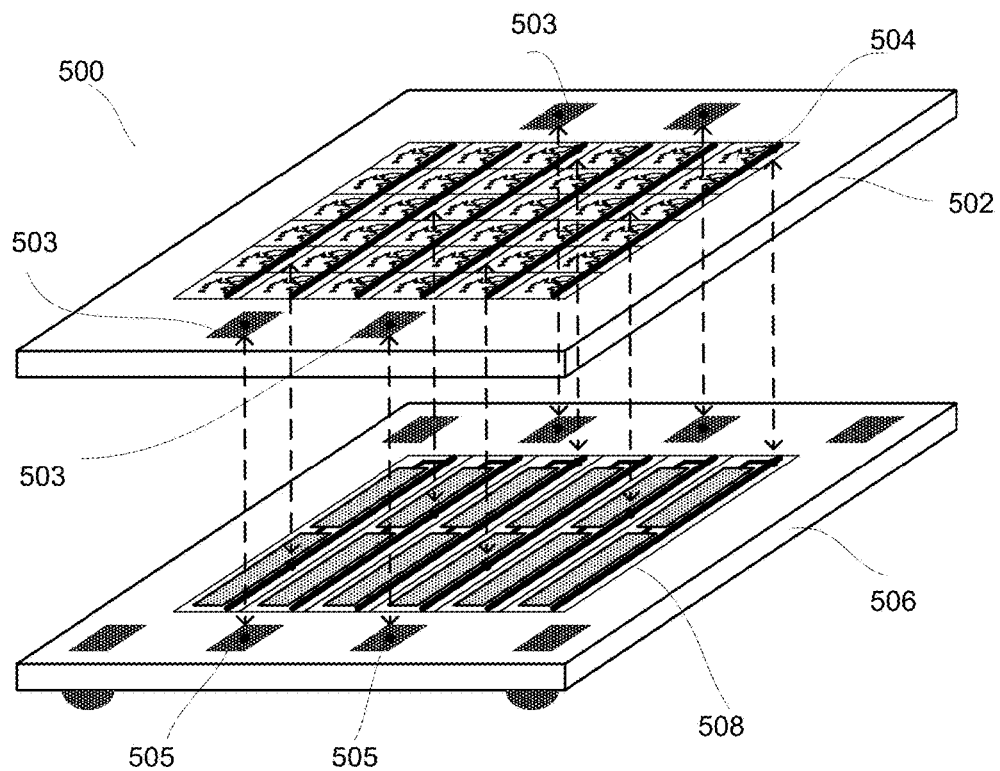
FIGS. 5A and 5B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 5B:
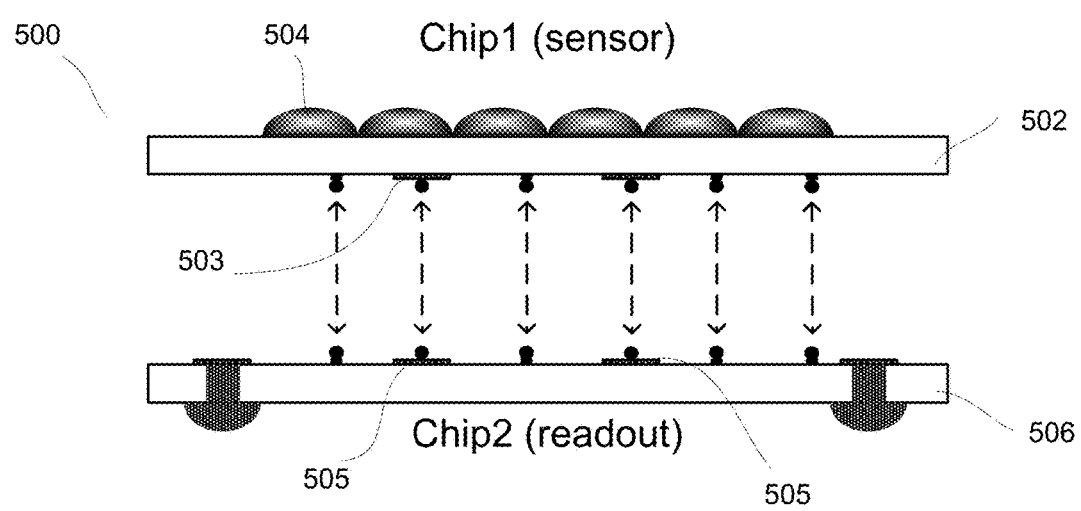

FIGS. 5A and 5B illustrate a perspective view and a side view, respectively, of an implementation of an imaging sensor 500 built on a plurality of substrates. As illustrated, a plurality of pixel columns 504 forming the pixel array are located on the first substrate 502 and a plurality of circuit columns 508 are located on a second substrate 506. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 502 of the two substrates/chips may be processed using an image CMOS process. The first substrate/chip 502 may be comprised either of a pixel array exclusively or a pixel array surrounded by limited circuitry. The second or subsequent substrate/chip 506 may be processed using any process, and does not have to be from an image CMOS process. The second substrate/chip 506 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 502 may be stacked with the second or subsequent substrate/chip 506 using any three-dimensional technique. The second substrate/chip 506 may support most, or a majority, of the circuitry that would have otherwise been implemented in the first image CMOS chip 502 (if implemented on a monolithic substrate/chip) as peripheral circuits and therefore have increased the overall system area while keeping the pixel array size constant and optimized to the fullest extent possible. The electrical connection between the two substrates/chips may be done through interconnects 503 and 505, which may be wirebonds, bump and/or TSV (Through Silicon Via).

Figure 6A:
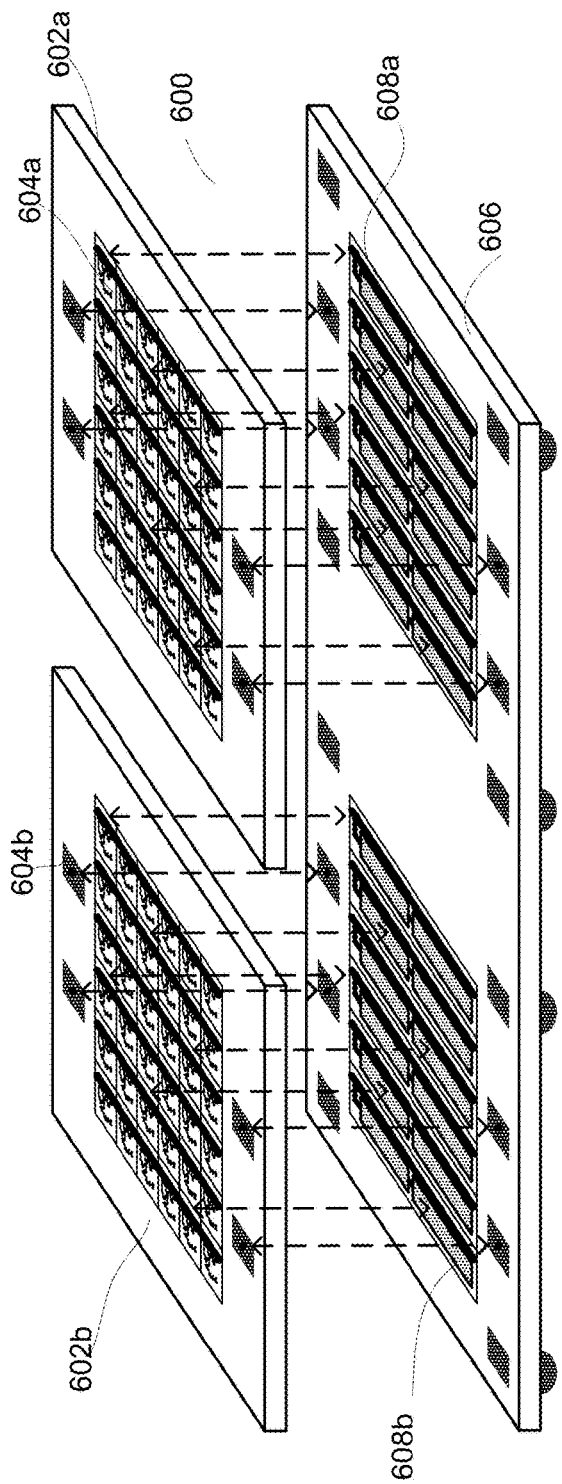
FIGS. 6A and 6B illustrate a perspective view and a side view, respectively, of an implementation of an imaging sensor having a plurality of pixel arrays for producing a three dimensional image, wherein the plurality of pixel arrays and the image sensor are built on a plurality of substrates.
Figure 6B:
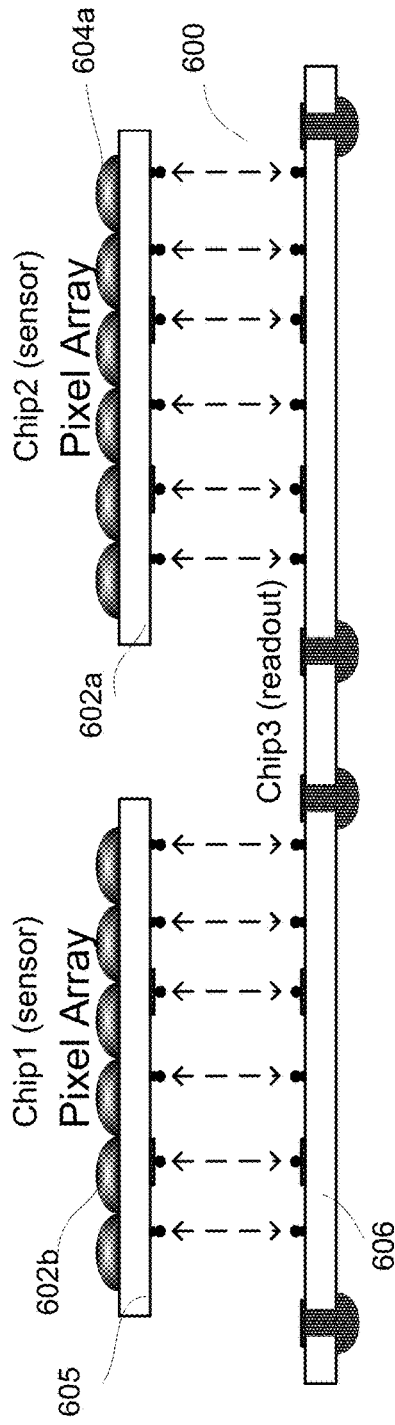

FIGS. 6A and 6B illustrate a perspective view and a side view, respectively, of an implementation of an imaging sensor 600 having a plurality of pixel arrays for producing a three dimensional image. The three dimensional image sensor may be built on a plurality of substrates and may comprise the plurality of pixel arrays and other associated circuitry, wherein a plurality of pixel columns 604a forming the first pixel array and a plurality of pixel columns 604b forming a second pixel array are located on respective substrates 602a and 602b, respectively, and a plurality of circuit columns 608a and 608b are located on a separate substrate 606. Also illustrated are the electrical connections and communications between columns of pixels to associated or corresponding column of circuitry.

Figure 7:
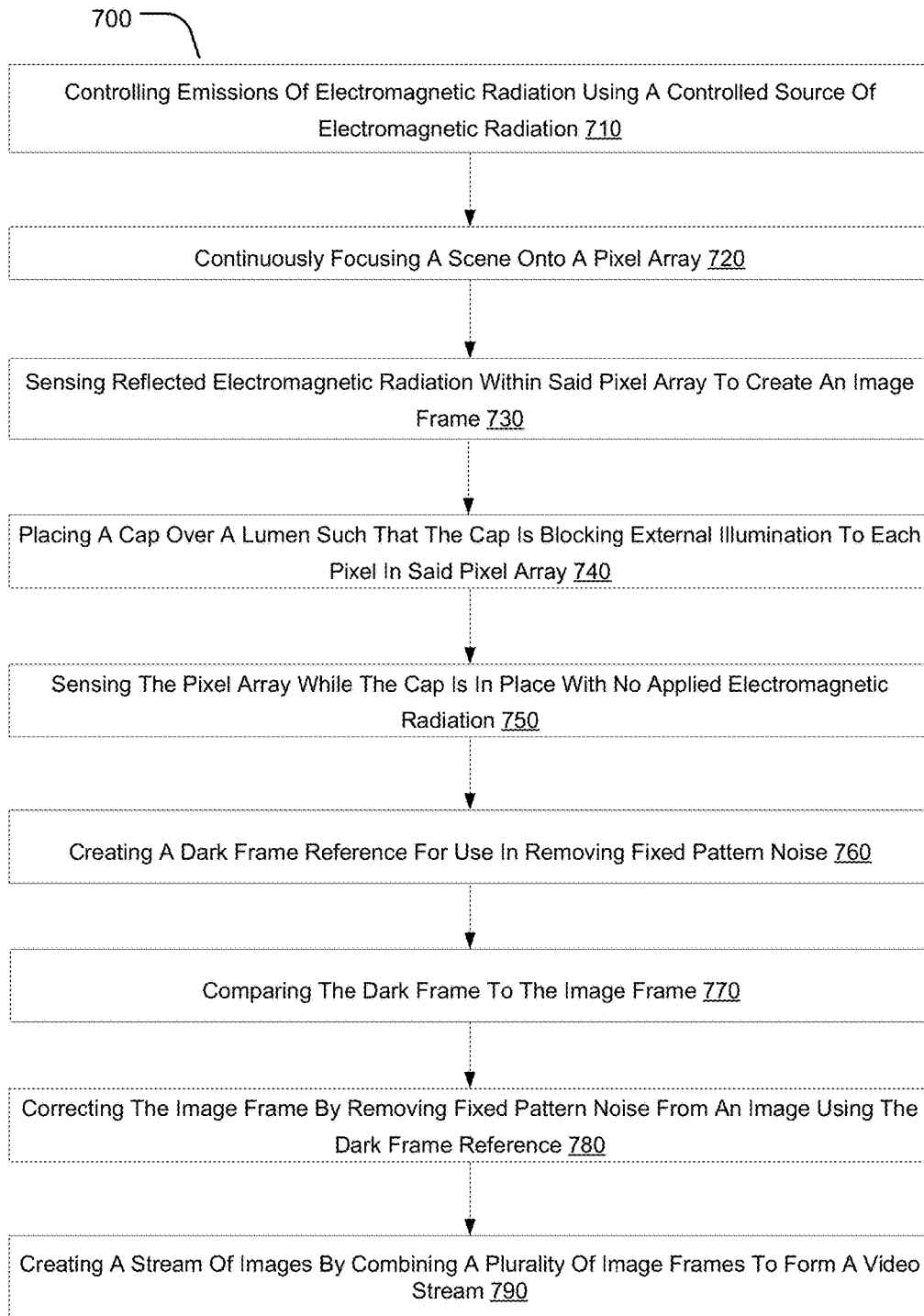
FIG. 7 is a flow chart illustrating an implementation of a system and method for adjusting white balance in accordance with the principles and teachings of the disclosure.
Figure 8:
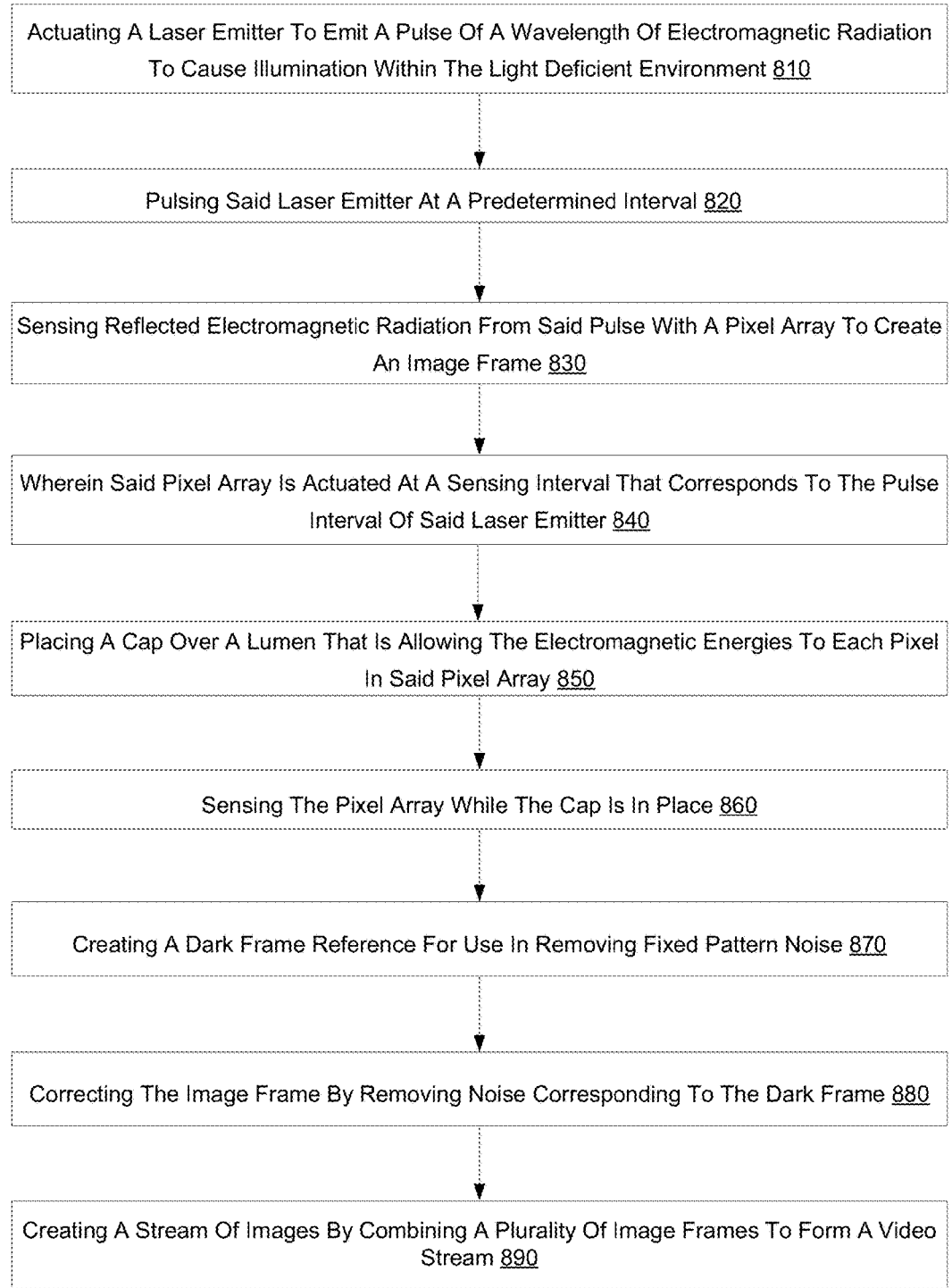
FIG. 8 is a flow chart illustrating an implementation of a system and method for adjusting white balance in accordance with the principles and teachings of the disclosure.
Figure 9:
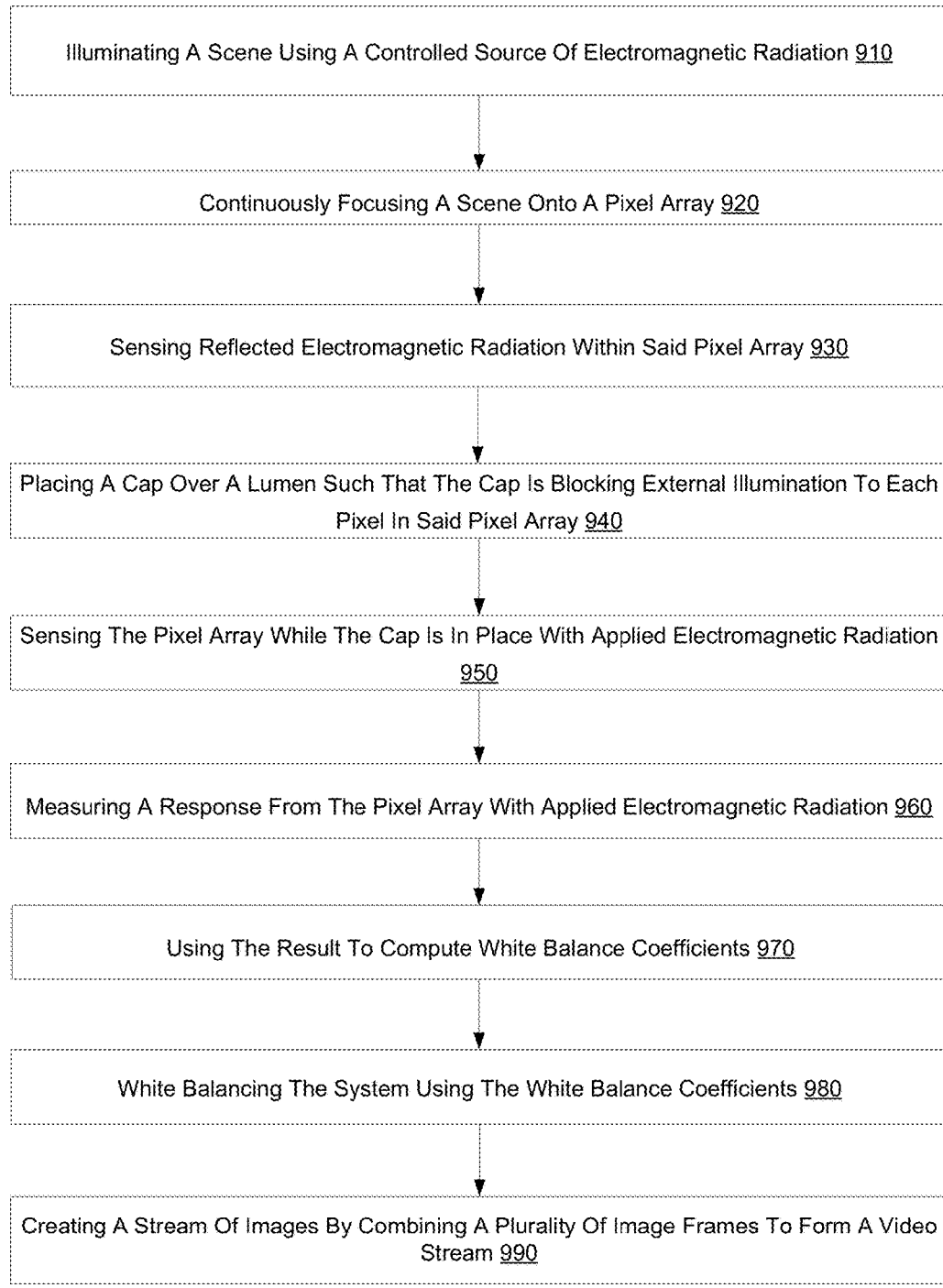
FIG. 9 is a flow chart illustrating an implementation of a system and method for adjusting white balance in accordance with the principles and teachings of the disclosure.

FIGS. 7-9 are flow charts illustrating implementations of a system and method for adjusting white balance in accordance with the principles and teachings of the disclosure.

The system and method 700 of FIG. 7 for adjusting fixed pattern noise in a digital imaging process for use with an endoscope in ambient light deficient environments may comprise controlling emissions of electromagnetic radiation using a controlled source of electromagnetic radiation at 710. At 720, the system and method 700 may continuously focus a scene onto a pixel array. At 730, the system and method 700 may comprise sensing reflected electromagnetic radiation with the pixel array to create an image frame. At 740, the system and method 700 may comprise placing a cap over a lumen such that the cap is blocking external illumination to each pixel in the pixel array. At 750, the system and method 700 may comprise sensing the pixel array while the cap is in place with no applied electromagnetic radiation. At 760, the system and method 700 may comprise creating a dark frame reference for use in removing fixed pattern noise. At 770, the system and method 700 may comprise comparing the dark frame reference to the image frame. At 780, the system and method 700 may comprise correcting the image frame by removing fixed pattern noise from an image using the dark frame reference. At 790, the system and method 700 may comprise creating a stream of images by combining a plurality of image frames to form a video stream.

The system and method 700 may comprise actuating an emitter to emit a pulse of a wavelength of electromagnetic radiation to cause illumination within the light deficient environment. In an implementation, the pulse may be within a wavelength range that comprises a portion of the electromagnetic spectrum. In an implementation, the emitter may be a laser emitter and the system and method 700 may further comprise pulsing the laser emitter at a predetermined interval. In an implementation, the method may further comprise actuating a pixel array at a sensing interval that corresponds to the pulse interval of the laser emitter.

The system and method 700 may comprise creating a dark frame from a single sensing of the pixel array while the cap is in place. It will be appreciated that in an implementation, a plurality of dark frames may be created from a plurality of sensing the pixel array while the cap is in place. In an implementation, the dark frames may be created upon startup of a system and stored within memory associated with the system.

In an implementation, the system and method 700 may comprise creating a dark frame after the pixel array is at operating temperature. In an implementation, the dark frame may be created after a surgical procedure has begun. In an implementation, the dark frame may comprise a plurality of dark frames that are created as part of the image frame stream by not applying electromagnetic radiation at given times and stored within memory associated with the system.

The system and method 700 may comprise a plurality of caps that correspond and are opaque to the emitted electromagnetic radiation.

The system and method 700 may comprise a response of the pixel array that corresponds to a photo-signal generated under controlled monochromatic radiation. In an implementation, the system and method 700 may comprise a response of the pixel array corresponds to the photo-signal generated under a plurality of wavelengths of radiation. In an implementation, a response of the pixel array corresponds to the photo-signal generated under a continuous spectrum of wavelengths of radiation.

The system and method 800 of FIG. 8 for adjusting fixed pattern noise in a digital imaging process for use with an endoscope in ambient light deficient environments may comprise actuating a laser emitter to emit a pulse of a wavelength of electromagnetic radiation to cause illumination within the light deficient environment at 810. At 820, the system and method 800 may pulse the laser emitter at a predetermined interval. At 830, the system and method 800 may comprise sensing reflected electromagnetic radiation from the pulse with a pixel array to create an image frame. At 840, the system and method 800 may comprise actuating the pixel array at a sensing interval that corresponds to the pulse interval of the laser emitter. At 850, the system and method 800 may comprise placing a cap over a lumen that is allowing or permitting the electromagnetic energies to each pixel in the pixel array. At 860, the system and method 800 may comprise sensing the pixel array while the cap is in place. In an implementation, sensing the pixel array while the cap is in place includes sensing with no applied electromagnetic radiation. At 870, the system and method 800 may comprise creating a dark frame reference for use in removing fixed pattern noise. At 880, the system and method 800 may comprise correcting the image frame by removing noise corresponding to the dark frame reference. At 890, the system and method 800 may comprise creating a stream of images by combining a plurality of image frames to form a video stream.

The system and method 900 of FIG. 9 for adjusting white balance in a digital imaging process for use with an endoscope in ambient light deficient environments may comprise illuminating a scene using a controlled source of electromagnetic radiation at 910. At 920, the system and method 900 may comprise continuously focusing the scene onto a pixel array. At 930, the system and method 900 may comprise sensing reflected electromagnetic radiation sensed by the pixel array. At 940, the system and method 900 may comprise placing a cap over a lumen, such that the cap is blocking external illumination to each pixel in the pixel array. At 950, the system and method 900 may comprise sensing the pixel array while the cap is in place with applied electromagnetic radiation. At 960, the system and method 900 may comprise measuring a response from the pixel array with applied electromagnetic radiation and outputting a result in memory. At 970, the system and method 900 may comprise using the result to compute white balance coefficients. At 980, the system and method 900 may comprise white balancing the system using the white balance coefficients. At 990, the system and method 900 may comprise creating a stream of images by combining a plurality of image frames to form a video stream.

In an implementation, the system and method 900 may comprise a plurality of caps that correspond and are opaque to the emitted electromagnetic radiation.

In an implementation, a response of the pixel array may correspond to a photo-signal generated under controlled monochromatic radiation. In an implementation, a response of the pixel array corresponds to the photo-signal generated under a plurality of wavelengths of radiation. In an implementation, a response of the pixel array corresponds to the photo-signal generated under a continuous spectrum of wavelengths of radiation.

In an implementation, the endoscope may be a reusable endoscopic device. In an implementation, the endoscope is a limited use endoscopic device. In an implementation, the endoscope is a re-posable use endoscopic device. In an implementation, the endoscope is a single-use endoscopic device.

In an implementation, the system and method 900 may comprise actuating a laser emitter to emit a pulse of a wavelength of electromagnetic radiation to cause illumination within the light deficient environment. In an implementation, the pulse is within a wavelength range that comprises a portion of the electromagnetic spectrum. In an implementation, the system and method 900 may further comprise pulsing the laser emitter at a predetermined interval. In an implementation, the system and method 900 may comprise actuating a pixel array at a sensing interval that corresponds to the pulse interval of said laser emitter.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

It will be appreciated that various features disclosed herein provide significant advantages and advancements in the art. The following embodiments are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

What is claimed is:

1. A method for adjusting fixed pattern noise in a digital imaging process for use with an endoscope in ambient light deficient environments comprising:
providing, during a training period, a cap that fits over a lumen of the endoscope such that the cap is blocking external illumination to each pixel in a pixel array, the lumen comprising an elongated lumen mechanically coupled to a handle for manipulation of the lumen during a surgical procedure;
creating, during the training period a first dark frame reference for use in removing fixed pattern noise while the cap is in place with no applied electromagnetic radiation and at a quiescent operating temperature for the endoscope during the training period;
removing the cap from the lumen at the quiescent operating temperature for the endoscope;
in response to removing the cap from the lumen, sensing electromagnetic radiation with said pixel array to create an image frame; and
correcting the image frame by removing fixed pattern noise from an image using the first dark frame reference.

2. The method of claim 1, wherein the method further comprises actuating an emitter to emit a pulse of a wavelength of electromagnetic radiation to cause illumination within the light deficient environment.

3. The method of claim 2, wherein said pulse is within a wavelength range that comprises a portion of the electromagnetic spectrum.

4. The method of claim 3, wherein said emitter is a laser emitter and wherein the method further comprises pulsing said laser emitter at a predetermined interval.

5. The method of claim 4, wherein the method further comprises actuating a pixel array at a sensing interval that corresponds to the pulse interval of said laser emitter.

6. The method of claim 1, wherein the first dark frame is created from a single sensing of the pixel array while the cap is in place.

7. The method of claim 1, wherein a plurality of dark frames are created from a plurality of sensing the pixel array while the cap is in place.

8. The method of claim 7, wherein said dark frames are created upon startup of a system and stored within memory associated with the system.

9. The method of claim 1, wherein the first dark frame is created before the surgical procedure has begun, the method further comprising;
in response to removing the cap from the lumen, beginning the surgical procedure using the endoscope;
placing the cap on the lumen after beginning the surgical procedure;
in response to placing the cap on the lumen, creating a second dark frame reference for use in removing fixed pattern noise while the cap is in place after the surgical procedure has begun with no applied electromagnetic radiation; and
correcting the image frame by removing fixed pattern noise from an image using the second dark frame reference.

10. The method of claim 1, wherein the first dark frame comprises a plurality of dark frames that are created as part of the image frame stream by not applying electromagnetic radiation at given times and stored within memory associated with the system.

11. The method of claim 1, wherein sensing electromagnetic radiation comprises sensing controlled monochromatic radiation to generate the image frame.

12. The method of claim 1, wherein sensing electromagnetic radiation comprises sensing under a plurality of wavelengths of radiation to generate the image frame.

13. The method of claim 1, wherein sensing electromagnetic radiation comprises sensing under a continuous spectrum of wavelengths of radiation to generate the image frame.

14. A system for digital imaging for use in ambient light deficient environments comprising:
an endoscope comprising a lumen and an image sensor, wherein the image sensor comprises a pixel array that senses electromagnetic radiation, the lumen comprising an elongated lumen mechanically coupled to a handle for manipulation of the lumen during a surgical procedure;
a cap configured to selectively cover a distal end of the lumen to block external illumination to each pixel in said pixel array;
a camera control unit in electrical communication with the image sensor;
wherein the image sensor creates a dark frame reference, during a training period, for use in removing fixed pattern noise while the cap is in place with no applied electromagnetic radiation at a quiescent operating temperature for the endoscope during the training period, and in response to removing the cap from the lumen at the quiescent operating temperature for the endoscope during the training period, senses electromagnetic radiation with said pixel array to create an image frame; and
wherein the camera control unit corrects the image frame by removing fixed pattern noise from an image using the dark frame reference.

15. The system of claim 14, wherein a dark frame is created from a single sensing of the pixel array while the cap is covering the distal end.

16. The system of claim 14, wherein the cap is sized and shaped to fit snuggly onto the lumen.

17. The system of claim 14, wherein the cap is made of a compliant material.

18. The system of claim 14, wherein the cap is opaque to the electromagnetic radiation emitted by an emitter.

19. The system of claim 14, wherein the endoscope is a reusable endoscopic device.

20. The system of claim 14 wherein the endoscope is a limited use endoscopic device.

21. The system of claim 14, wherein the endoscope is a re-posable use endoscopic device.

22. The system of claim 14, wherein the endoscope is a single-use endoscopic device.

23. A method for adjusting fixed pattern noise in a digital imaging process for use with an endoscope in ambient light deficient environments comprising:
- providing, during a training period, a cap that fits over a lumen of the endoscope such that the cap is blocking external illumination to each pixel in a pixel array, wherein the lumen comprises a lumen mechanically coupled to a handle for manipulation of the lumen during a surgical procedure;
- creating a dark frame reference, during a training period, for use in removing fixed pattern noise while the cap is in place with no applied electromagnetic radiation at a quiescent operating temperature for the endoscope during the training period;
- illuminating, during the training period, an interior of the cap using a controlled source of electromagnetic radiation;
- determining, during the training period white balance coefficients while the cap is in place and during illumination of the interior by a source of electromagnetic illumination at a quiescent operating temperature for the endoscope during the training period;
- removing the cap from the lumen at the quiescent operating temperature for the endoscope;
- in response to removing the cap from the lumen, sensing electromagnetic radiation with said pixel array to create an image frame; and
- correcting the image frame using the dark frame reference and the white balance coefficients.

24. The method of claim 23, wherein sensing electromagnetic radiation comprises sensing controlled monochromatic radiation to generate the image frame.

25. The method of claim 23, wherein sensing electromagnetic radiation comprises sensing under a plurality of wavelengths of radiation to generate the image frame.

26. The method of claim 23, wherein sensing electromagnetic radiation comprises sensing under a continuous spectrum of wavelengths of radiation to generate the image frame.

27. The method of claim 23, wherein the endoscope is a reusable endoscopic device.

28. The method of claim 23, wherein the endoscope is a limited use endoscopic device.

29. The method of claim 23, wherein the endoscope is a re-posable use endoscopic device.

30. The method of claim 23, wherein the endoscope is a single-use endoscopic device.

31. The method of claim 23, wherein the controlled source of electromagnetic radiation comprises a laser emitter, the method further comprising emitting a pulse of a wavelength of electromagnetic radiation to cause illumination within the light deficient environment, wherein sensing electromagnetic radiation to create the image frame comprises sensing during the emitting the pulse.

32. The method of claim 31, wherein the method further comprises pulsing said laser emitter at a predetermined interval.

33. The method of claim 32, wherein the method further comprises sensing electromagnetic radiation using the pixel array at a sensing interval that corresponds to the pulse interval of the laser emitter.

34. A system for digital imaging for use in ambient light deficient environments comprising:
- an endoscope comprising a lumen and an image sensor, wherein the image sensor comprises a pixel array that senses electromagnetic radiation, the lumen comprising an elongated lumen mechanically coupled to a handle for manipulation of the lumen during a surgical procedure;
- a cap configured to selectively cover a distal end of the lumen to block external illumination to each pixel in said pixel array;
- a camera control unit in electrical communication with the image sensor and comprising one or more of a processor and memory to control that cause the image sensor to:
  - create a dark frame reference, during a training period, for use in removing fixed pattern noise while the cap is in place with no applied electromagnetic radiation at a quiescent operating temperature for the endoscope during the training period;
  - determining white balance coefficients based on a white reference frame captured while the cap is in place and during illumination of the interior of the cap by a source of electromagnetic radiation at the quiescent operating temperature for the endoscope during the training period; and
  - in response to removing the cap from the lumen at the quiescent operating temperature for the endo scope during the training period, correct an image frame by removing fixed pattern noise from an image using the dark frame reference and correcting the image frame using the white balance coefficients.

* * * * *